US009519981B2

(12) United States Patent
Sudarsky et al.

(10) Patent No.: US 9,519,981 B2
(45) Date of Patent: Dec. 13, 2016

(54) VISUALIZING BRAIN NETWORK CONNECTIVITY

(75) Inventors: Sandra Sudarsky, Bedminster, NJ (US); Mariappan S. Nadar, Plainsboro, NJ (US); Shanhui Sun, Iowa city, IA (US); Alban Lefebvre, Jersey City, NJ (US); Bernhard Geiger, Cranbury, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 576 days.

(21) Appl. No.: 13/539,863

(22) Filed: Jul. 2, 2012

(65) Prior Publication Data

US 2013/0113816 A1    May 9, 2013

Related U.S. Application Data

(60) Provisional application No. 61/555,571, filed on Nov. 4, 2011.

(51) Int. Cl.
*G09G 5/02* (2006.01)
*G06T 11/20* (2006.01)
*A61B 5/00* (2006.01)

(52) U.S. Cl.
CPC ............ *G06T 11/206* (2013.01); *A61B 5/0042* (2013.01); *A61B 5/4064* (2013.01)

(58) Field of Classification Search
CPC ............... G01N 33/57449; G01N 2800/36; G05B 15/02; G06K 9/00369; G06K 9/00523; G06K 2209/01; G06T 11/008; G06T 2200/04; G06T 11/206; G06T 2207/10088; A61B 5/0042; A61B 5/4064; G06F 19/345; G06F 17/18; G06Q 10/0631; Y10S 707/99931

USPC .......................................................... 345/589
See application file for complete search history.

(56) References Cited

U.S. PATENT DOCUMENTS

| 8,484,144 B2 * | 7/2013 | Rhodes ........................ 706/15 |
| 8,614,708 B2 * | 12/2013 | Winnemoeller ...... G06T 11/001 345/423 |
| 2007/0180408 A1 * | 8/2007 | Rusu et al. ................... 715/855 |

(Continued)

FOREIGN PATENT DOCUMENTS

NL    WO2011128823    * 10/2011 ............. G06F 19/00

OTHER PUBLICATIONS

"Visualizing and exploring profiles with calling context ring charts," published online Jul. 8, 2010 in Wiley InterScience (www.interscience.wiley.com), DOI: 10.1002/spe.985 by Philippe Moret et al.*

(Continued)

*Primary Examiner* — Gregory J Tryder
*Assistant Examiner* — Kwang Lee (57) ABSTRACT

A method for visualizing brain connectivity includes receiving image data including molecular diffusion of brain tissue, constructing a tree data structure from the image data, wherein the tree data structure comprises a plurality of network nodes, wherein each network node is connected to a root of the tree data structure, rendering a ring of a radial layout depicting the tree data structure, wherein a plurality of vertices may be traversed from the top to the bottom, duplicating at least one control point for spline edges sharing a common ancestor, and bundling spline edges by applying a global strength parameter β.

20 Claims, 4 Drawing Sheets

(56) References Cited

U.S. PATENT DOCUMENTS

2013/0035922 A1* 2/2013 Martens .............. G06F 19/3437
                                                                                  703/11

OTHER PUBLICATIONS

"Hierarchical Edge Bundles: Visualization of Adjacency Relations in Hierarchical Data" published on IEEE Transactions on Visualization and Computer Graphics, vol. 12, No. 5, Sep./Oct. 2006 by Danny Holten.*

* cited by examiner

VISUALIZING BRAIN NETWORK CONNECTIVITY

CROSS-REFERENCE TO RELATED APPLICATION

This is a non-provisional application claiming the benefit of U.S. provisional application Ser. No. 61/555,571, filed Nov. 4, 2011, the contents of which are incorporated by reference herein in their entirety.

BACKGROUND

1. Technical Field

The present disclosure relates to visualization tools, and more particularly to methods for visualizing brain network connectivity.

2. Discussion of Related Art

Regarding brain network mapping and analysis, the brain can be parcellated into distinct modules (regions), which have distinct connectivity patterns. Network nodes represent regions of the brain and edges indicate relations between nodes. An edge may represent a structural relation in a network or a functional relation in a network depending on underlying images.

Scientific observation via visualization helps researchers discover new knowledge about brain connectivity.

BRIEF SUMMARY

According to an embodiment of the present disclosure, a method for visualizing brain network connectivity includes receiving image data corresponding to a brain of interest, constructing a tree data structure from the image data, wherein the tree data structure comprises a plurality of network nodes, wherein each network node is connected to a root of the tree data structure, rendering a ring of a radial layout depicting the tree data structure, wherein a plurality of vertices may be traversed from the top to the bottom, duplicating at least one control point for spline edges sharing at a common ancestor, bundling spline edges by applying a global strength parameter $\beta$, and displaying a visualization of brain network connectivity in the radial layout including bundled spline edges.

According to an embodiment of the present disclosure, a method for visualizing brain network connectivity includes receiving image data corresponding to a brain of interest, constructing a tree data structure from the image data, wherein the tree data structure comprises a plurality of network nodes, wherein each network node is connected to a root of the tree data structure, rendering a ring of a radial layout depicting the tree data structure, wherein a plurality of vertices may be traversed from the top to the bottom, duplicating at least one control point for spline edges sharing at a common ancestor, and bundling spline edges by applying a global strength parameter $\beta$.

According to an embodiment of the present disclosure, a method for visualizing brain network connectivity includes receiving image data corresponding to a brain of interest, constructing one of a structural and a functional tree data structure from the image data, wherein a tree data structure comprises a plurality of network nodes, wherein each network node is connected to a root of the tree data structure, displaying the tree data structure as a ring of a radial layout including the spine edges, duplicating at least one control point for a plurality of spline edges sharing a common ancestor, bundling the spline edges into a plurality of bundles according to the molecular diffusion of the brain of interest, and displaying a visualization of brain network connectivity in the radial layout including bundled spline edges.

According to an embodiment of the present disclosure, a method for visualizing brain network connectivity is embodied in a computer program product including instructions executable by a processor.

BRIEF DESCRIPTION OF THE DRAWINGS

Preferred embodiments of the present disclosure will be described below in more detail, with reference to the accompanying drawings.

DETAILED DESCRIPTION OF PREFERRED EMBODIMENTS

According to an embodiment of the present disclosure, a 2D/3D (two-dimensional/three-dimensional) hybrid brain network user interface is described for interactive visualization of brain connectivity.

According to an embodiment of the present disclosure, a 2D visualization of brain connectivity may be displayed in a radial layout, a matrix layout (e.g., adjacency matrix), etc. The visualization may reveal a coordinate dependent network of a brain of interest using a clutter reduction technique.

According to an embodiment of the present disclosure, a 3D visualization of the brain connectivity may be shown on top of an anatomical structure. The anatomical structure may include a visualization of network connections, fiber pathways, multiplanar reformatted planes (MPR), isosurface rendering, etc. That is, according to an embodiment of the present disclosure, a system incorporates volume rendering, orthogonal multiplanar reformatted (MPR) planes and isosurface rendering for better understanding anatomical structure.

In view of the foregoing, in a multi-window or multi-display system including two views of the data having both 2D and 3D brain network interfaces/visualizations allows for interaction on a 2D visualization and observation of a result on a 3D visualization.

According to an embodiment of the present disclosure, image data may be obtained by various methods. These methods may include molecular diffusion, resting-state functional magnetic resonance imaging (fMRI), magnetoencephalography (MEG)/electroencephalography (EEG) and the like. For example, fMRI uses the paramagnetic properties of oxygenated and deoxygenated hemoglobin to see images of changing blood flow in the brain associated with neural activity. This allows images to be generated that show activated brain structures given different tasks. In another example, MEG measures magnetic fields produced by electrical activity in the brain.

Referring now to an exemplary 2D/3D hybrid brain network visualization, a method for visualizing brain networks includes placing nodes at a centroid, or geometric center, of a brain region they represent and using straight lines to display edges between the nodes.

According to an embodiment of the present disclosure, a 3D brain network edge bundling method may be used to reduce clutter. A hierarchy may be defined based on well-known brain atlases or generated algorithmically. The hierarchy may be used to facilitate the bundling. For example, a hierarchy edge bundling (HEB) method may be extended to facilitate bundling.

HEB may be used in conjunct on with existing tree visualization techniques to enable users to choose from among different tree visualizations (e.g., rooted tree, radial tree, balloon tree, or tree map layout) and to facilitate integration into other tools. HEB may reduce visual clutter when dealing with adjacency edges HEB may also be used to control the strength of bundling. For example, lower bundling strength may be used to provide low-level, node-to-node connectivity information, whereas higher bundling strength may be used to provide high-level information.

A 2D HEB method may be applied to hierarchical structures, wherein edges are rendered using B-Spline curves. Each B-Spline curve may be guided by the hierarchical structure. Edges started from leaf nodes and then converge towards ancestor tree nodes. B-Spline curves at a location of shared ancestors may be bundled and gradually diverged at location of leaf nodes. A global bundling strength parameter β may be used. The strength parameter may by defined as β∈[0,1].

It should be noted that the present disclosure is not limited to B-Splines and that other curves may be used, for example, Beta-splines.

Figure 1A:
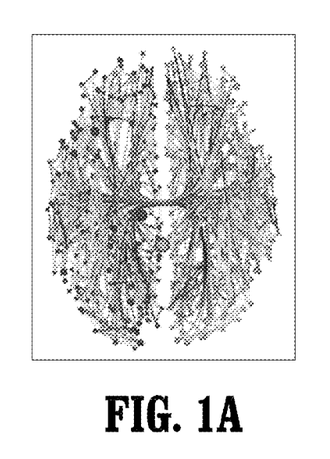
FIGS. 1A-C show edge drawings for visualizing brain network connectivity according to embodiments of the present disclosure.
Figure 1B:
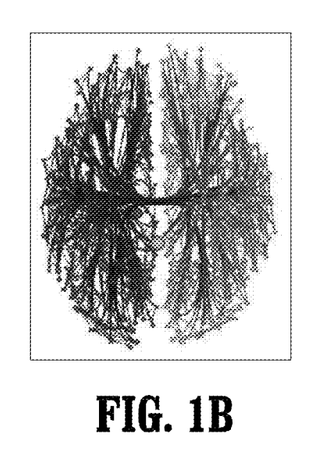
Figure 1C:
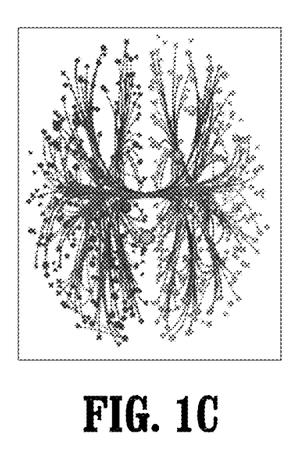

Referring to FIG. 1A-C, exemplary edge drawings are shown in which the size of a node is proportional to the number of connections. In FIG. 1A, the edge drawing uses weighted connections with different colors indicating different strength connections, e.g., red may be a strong connection while blue may indicate a weak connection. In FIG. 1A, a 3D HEB based edge drawing is shown using weighted connections. In FIG. 1B, a 3D HEB based edge drawing is shown using alpha blending. In FIG. 1C, a result of thresholding the image of FIG. 1A is shown. For example, a threshold for the strength of the connections may be used, wherein only edges with strength higher than certain value may be shown.

Figure 2:
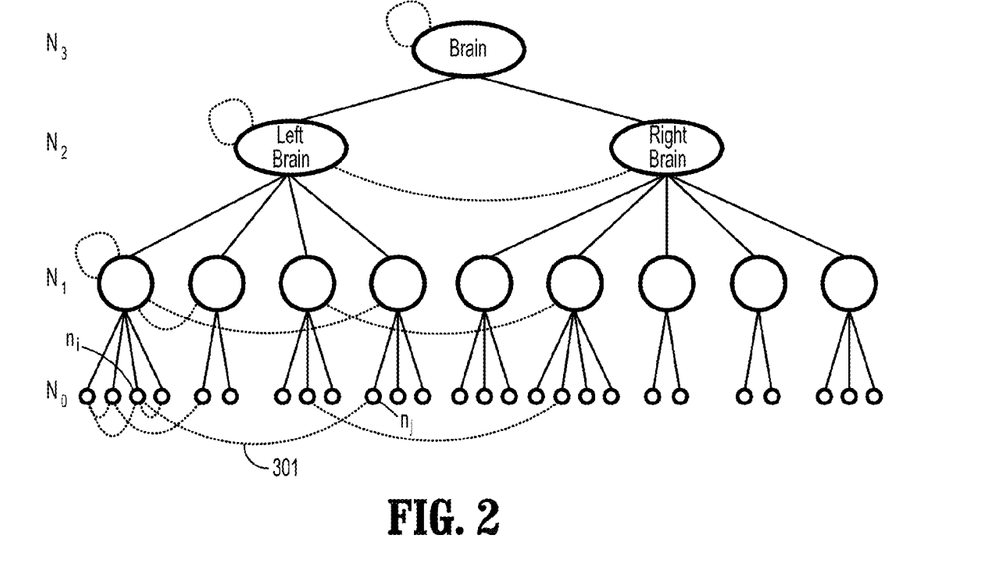
FIG. 2 is a hierarchical structure according to embodiments of the present disclosure.

Referring now to the clustering of edges, structural and functional brain networks exhibit a hierarchical structure as depicted in FIG. 2.

Structural brain networks or structural connectivity may refer to a network of physical or synaptic connections linking sets of neurons or neuronal elements in some brain tissue of interest. A structural brain network may also reveal structural biophysical attributes such as synaptic strength or effectiveness.

Functional brain networks or functional connectivity may be determined as a statistical measure of deviations from statistical independence between distributed and potentially spatially remote neuronal units. Statistical dependence may be estimated by measuring correlation or covariance, spectral coherence or phase-locking. Functional brain networks may reveal a degree of left-right hemispherical asymmetry in language and memory regions of the brain, to check the neural correlates of a seizure, to study how the brain recovers from a stroke, to test the efficacy of a drug or a behavioral therapy, to detect disease and disorder, etc.

Knowledge of the structural and functional brain networks may be utilized in a 3D HEB method. Network nodes may be clustered recursively. This clustering may be performed in on-line or off-line steps. Clustering methods may be implemented semi-automatically and fully automatically.

In the semi-automatic method, an expert may cluster atlas regions into larger regions recursively and store hierarchy information. Network nodes derived from the same atlas will have corresponding stored hierarchy information.

In the fully automatic method, a network clustering method may be recursively applied on each network.

Regardless of the method used to generate the hierarchical clusters, centroids of the hierarchical clusters may be determined and used to construct the hierarchical brain networks $\{N_1, N_2, \ldots, N_n\}$ to guide the connections of the target network $N_0$, where 1 to n indicates clustering from the finest to the coarsest and the whole brain is used as the coarsest cluster.

Control points are used to build a B-Spline. For example, in FIG. 3B, an edge $(n_i, n_j)$ 301 in $N_0$ is represented by a cubic B-spline (see also FIG. 2). The control points may be found by searching a nearest common ancestor of two related nodes of $N_0$ from the network $N_1$ to $N_n$. Control points at a common ancestor are duplicated (e.g., 2 copies) to strengthen the bundle effectiveness. Local strength parameters $\{\beta_1, \beta_2, \ldots, \beta_n\}$ may be used to balance bundling.

Various methods may be used for controlling the curves. For example, in one method a control polygon may be straightened using control points $P_i$ and subsequently uses these control points $P_i'$ of the straightened control polygon as a new control polygon to generate a spline curve:

$$P_i' = \beta \cdot P_i + (1 - \beta)\left(P_0 + \frac{i}{N-1}(P_{N-1} - P_0)\right)$$

where N is a number of control points, i is a control point index $i \in \{0, \ldots, N-1\}$, and β is the bundling strength.

Another method for controlling the cures may be given for straightening each spline point S(t) when the curve is evaluated to create a new, straightened spline point S'(t) as follows:

$$S'(t) = \beta \cdot S(t) + (1-\beta)(P_0 + t(P_{N-1} - P_0))$$

Wherein t is the spline curve parameter, $t \in [0,1]$.

Figure 3A:
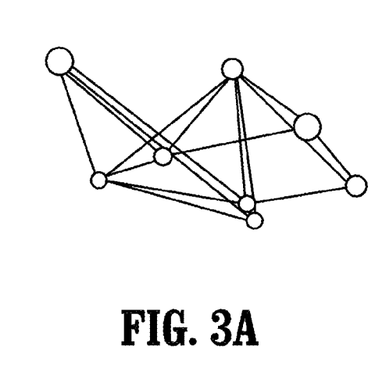
FIGS. 3A-C show different local bundling for nodes belonging to the finest cluster according to embodiments of the present disclosure.
Figure 3B:
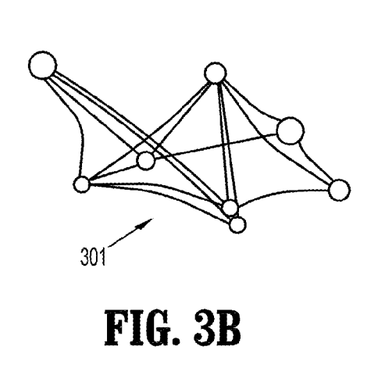
Figure 3C:
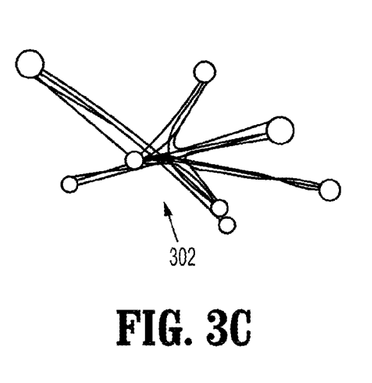

The effect of local strength parameter in a finest cluster, e.g., the target network $N_0$, is shown in the FIGS. 3A-C. In general, siblings in the finest cluster are near each other; too much bundling may form a star structure towards the centroid leading to clutter.

More particularly, FIGS. 3A-C show an effect of changing a local bundle parameter. In FIG. 3A, β=0, and no bundling effect is evident. In FIG. 3B, $\beta_1$=0.2, with a balanced bundling effect is obtained, wherein curved B-Splines (301) are evident. In FIG. 3C, $\beta_1$=0.98, with a bundling effect leads to star structure, wherein B-Splines between different nodes converge as a central point (302).

To indicate a binary connection relation, an alpha blending technique may be used to color edges. Alpha blending may be used to emphasize certain curves or bundles, e.g., short curves or bundles. Alpha blending may be used to adjust the opacity of different curves or bundles according to a parameter such as length.

A spline color is driven by vertex color buffer. Colors of the start and end nodes may be blended. Local blending factor may be a normalized distance to the start node and a global blending factor is the normalized line length.

A stereoscopic visualization technique may be applied in 3D visualization. To make the stereoscopic rendering portable to various display devices, two pass rendering may utilized. In a first pass, left/right view images may be rendered to frame buffer object (FBO) at full screen resolution. In a second pass, content from FBO as texture may be attached to corresponding viewer (e.g., quad buffer mode) or viewers (e.g., side by side, etc.). User interactions may be mapped to first pass framework.

Figure 4A:
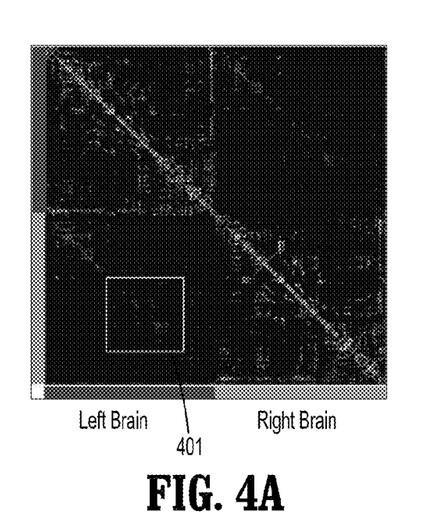
FIGS. 4A-B are examples of adjacency matrices according to embodiments of the present disclosure.
Figure 4B:
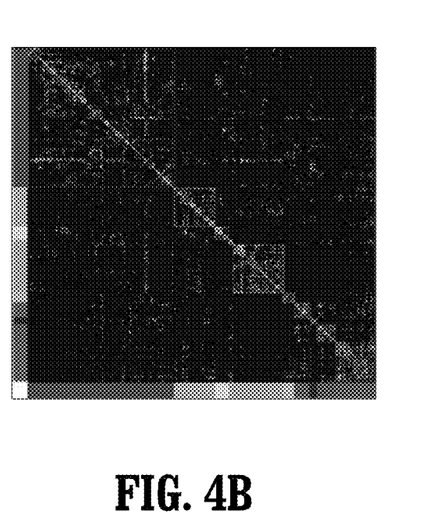

Referring to an exemplary 2D network visualization, an adjacency matrix, e.g., as shown in FIGS. 4A and 4B, may be used to depict how the nodes of a network are connected to each other. More particularly, FIG. 4A shows an atlas based clustering adjacency matrix and FIG. 4B shows an algorithmic based clustering adjacency matrix (e.g., showing clusters related by connectivity in the brain). The adjacency matrix may be interactive. For example, a node or set of nodes of the adjacency matrix can be selected on the matrix view to display edges adjacent to the selected node or nodes. In FIG. 4A, a set of nodes within a square 401 is shown as being selected, wherein all edges of the selected nodes may be displayed in a corresponding 3D view. Isosurfaces corresponding to the selected node can also be displayed.

The adjacency matrix allows for various tasks to be performed, such as finding if two nodes are connected, how strong their connections are, where dense and strong connections are found, etc. To overview the clustering method influence on the network, a series of reordered matrices may be used based on hierarchy information.

The hierarchical brain map provides a frame of reference that may be useable to understand the inter-connections between brain nodes. According to an embodiment of the present disclosure, the hierarchical brain map may be used to improve brain network visualization. For example, a 2D radial layout is an efficient tool to visualize the connections between brain regions. The 2D radial layout may enable a visualization of brain networks to help researchers understand how nodes are connected structurally and functionally. For example, the 2D radial layout can aid in the comparison of brain networks (e.g., people with brain injuries vs. healthy patients, older vs. young brains, etc.).

The 2D radial layout places nodes in centered concentric rings. For some or all nodes in the graph a radius is given. A radial layout may be generated using a 2D HEB technique. In this case, the map drawing may start from a leaf layer with a region text label displayed when the corresponding region is interacted, wherein a tree map indicates hierarchy structure intuitively.

Figure 5:
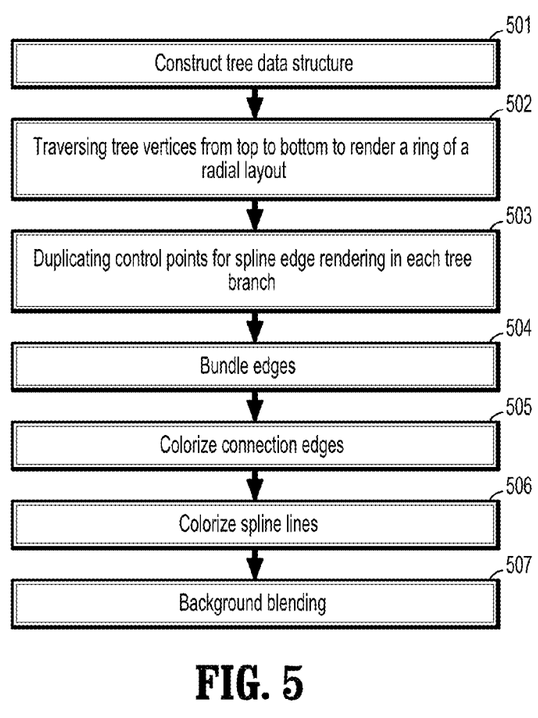
FIG. 5 is a flow diagram for visualizing brain network connectivity according to an embodiment of the present disclosure.

To improve the visual clarity, a 2D HEB technique may be used. According to an embodiment of the present disclosure, in a method for visualization (FIG. 5), a tree data structure is constructed (501). The top layer of the tree has one vertex, which corresponds the whole brain, vertices at a bottom layer corresponds to the network nodes, and vertices at remaining layers correspond to clustered regions. Every network node should be in the tree and have a path to the root. When rendering the ring of the radial layout, tree vertices may be traversed from the top to the bottom (502). The ring segment size is proportional to the number of vertices at bottom layer in the corresponding tree branch. For spline edge rendering the control points may be duplicated at a common ancestor (503). A global strength parameter β may be used to bundle edges (504). The mono color for connection edges may be utilized (505). Each spline line obtains the color value by linear interpolation using line length (506). In the black background, the OpenGL maximum blending may be turned on to make sure a short spline line is displayed when meeting a longer spline (507).

Navigating network nodes in 3D may not be convenient. According to an embodiment of the present disclosure, the matrix map and radial layout are interactive. For example, dragging a region of the matrix (e.g., by using an interaction device, such as a mouse or track-pad) produces corresponding edge display in the 3D node-link network. Clicking a cluster region of the reordered matrix may show corresponding cluster edges in 3D network. For the radial layout, the ring segment can be selected by the mouse. If the selected segment is on the most inner ring, the selected node's connections are displayed in both radial layout and 3D network. If a higher layer ring segment is selected, the nodes in this cluster and corresponding edges will act accordingly. In addition, an interactive color bar may be used to threshold weight connection.

Figure 6A:
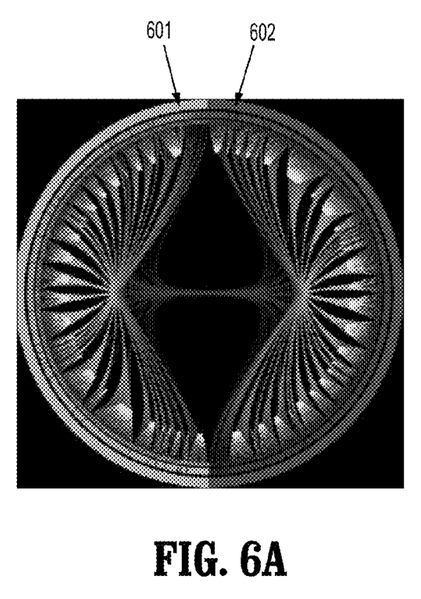
FIGS. 6A-B are examples of 2D HEB based radial layouts according to embodiments of the present disclosure.
Figure 6B:
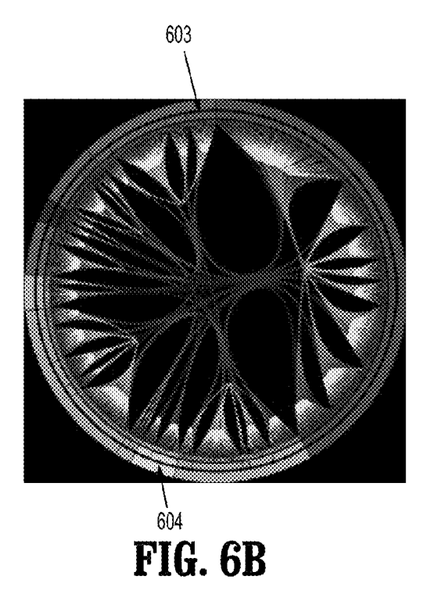

FIGS. 6A-B are examples of 2D HEB based radial layouts. The color of ring segment defined from the clusters in second top layer of the tree. In FIG. 6A, a semi-automatic clustering based hierarchy is shown. The visualization of FIG. 6A is based on an anatomical atlas. In FIG. 6A, different colors or shaping may correspond to the left and right brain hemispheres, for example, a blue color 601 corresponds to the right brain and a red color 602 corresponds to the left brain. Further, the radial layout includes concentric circles, each circle corresponding to a level of the underlying hierarchy, for example, the outer ring corresponds to the $N_2$ layer distinguished the different hemispheres (e.g., left brain from the right brain). A next concentric circle, disposed within the outer ring may correspond to the $N_1$ layer distinguishing different regions, and so on.

In FIG. 6B, a fully automatic clustering based hierarchy is shown. FIG. 6B is based on functional connections. In FIG. 6B, different colors or shading (e.g., 603 and 604) may correspond to different functional connections.

It should be understood that a visualization of brain network connectivity may be view together with images of a corresponding brain tissue. For example, the brain network connectivity and the brain tissue may be viewed together in different views. Furthermore, the selection of an area in one visualization may highlight a corresponding feature in another visualization.

According to an embodiment of the present disclosure, a fiber tracking method may used to detect fiber pathways in Diffusion Tensor Imaging (DTI) data by following directional information from diffusion tensors. These physical fibers correspond to white-matter connectivity while the connections obtained from fMRI data provide information about functional connectivity.

More particularly, an exemplary fiber tracking method may include the iterative steps of receiving initial data as a subset of voxels that have been selected by applying a threshold to Fractional Anisotropy (FA) values, finding a cluster of points with highly collinear diffusion directions, performing region growth to find suitable seed points in a plane that is normal to the cluster's mean direction, starting from the center of the cluster, and tracing the pathways from the seed points. In the initial subset of voxels, those voxels that are close enough to any of the pathways may be eliminated using a distance threshold. The method repeats a fixed number of iterations or until not enough voxels are left to define a cluster. The selection of voxels used as seed points may be stored to a computer readable media or displayed in a diffusion tensor visualization. These voxels constitute a minimal set of seed points yielding fiber pathways that can be used to visualize white-matter connectivity on the whole brain.

Figure 7:
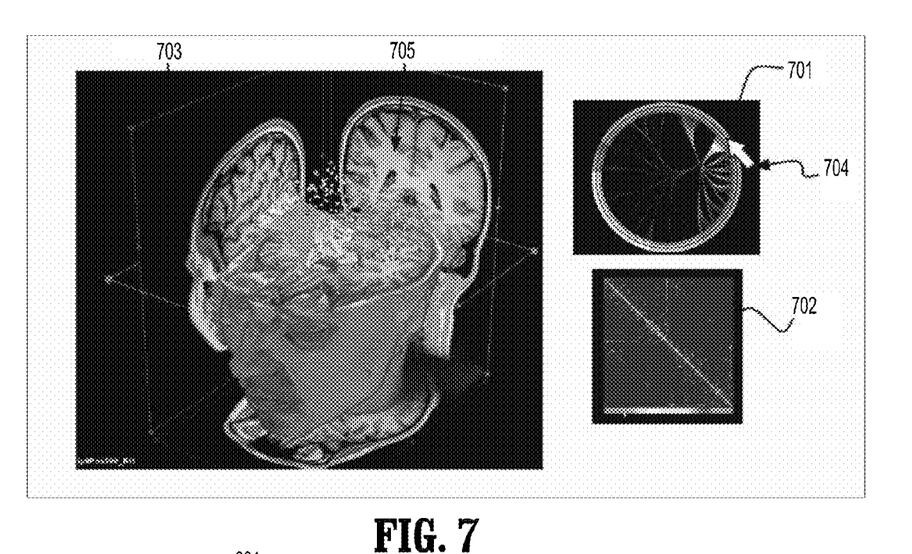
FIG. 7 is an exemplary 2D/3D fiber visualization according to embodiments of the present disclosure.

Referring to FIG. 7, in view of the foregoing, a 2D visualization, e.g., 701 and 702, according to an embodiment of the present disclosure may be displayed with a variety of 3D data, e.g., 703. In FIG. 7, a 3D fiber visualization 702 displays fibers may be associated with, or mapped to, selected nodes and or edges in the network. For example, these nodes and edges may be selected from the 2D visualization by a pointer 704 or other means of interaction, such as a touch screen. The relation between these two forms of connectivity, as well as others, can be explored using implementations of embodiments of the visualization tools described herein. Further, 2D slice data, e.g., 705, may be displayed automatically with a selection of certain data in any of the 2D or 3D views.

It is to be understood that embodiments of the present disclosure may be implemented in various forms of hardware, software, firmware, special purpose processors, or a combination thereof. In one embodiment, a software application program is tangibly embodied on a non-transitory computer-readable storage medium, such as a program storage device or computer-readable storage medium, with an executable program stored thereon. The application program may be uploaded to, and executed by, a machine comprising any suitable architecture.

Figure 8:
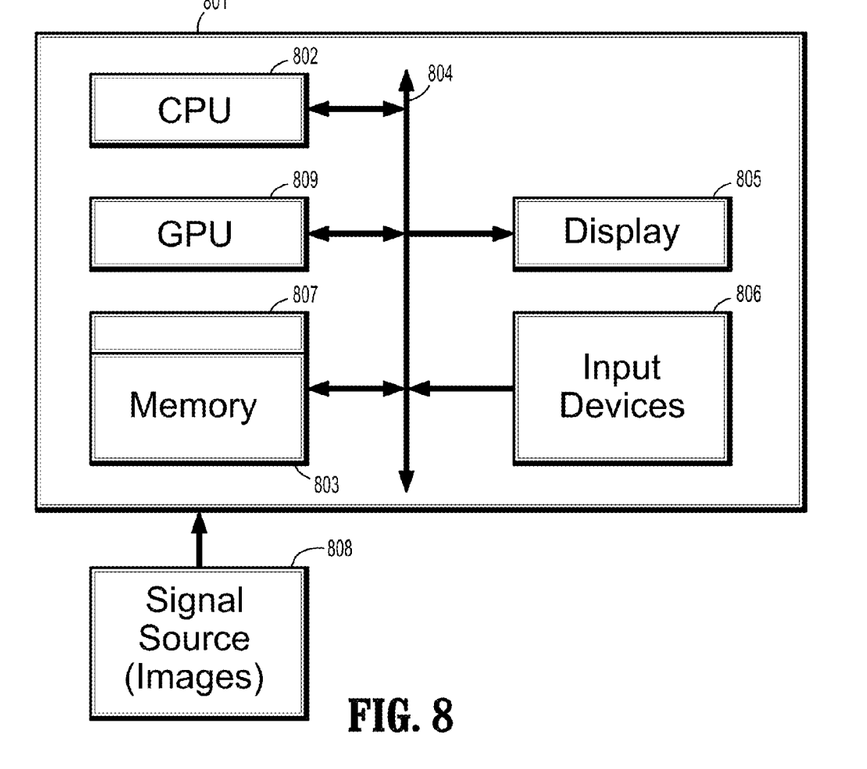
FIG. 8 is an exemplary system for performing a visualization of brain network connectivity according to an embodiment of the present disclosure.

Referring to FIG. 8, according to an embodiment of the present disclosure, a computer system (block 801) for visualizing brain network connectivity includes, inter alia, a CPU (block 802), a memory (block 803) and an input/output (I/O) interface (block 804). The computer system (block 801) is generally coupled through the I/O interface (block 804) to a display (block 805) and various input devices (block 806) such as a mouse, keyboard, medical scanners, power equipment, etc. The display (block 805) may be implemented to display the rules, e.g., as the rules evolve during evaluation, ranking and refinement or as an output set of rules. The support circuits can include circuits such as cache, power supplies, clock circuits, and a communications bus. The memory (block 803) can include random access memory (RAM), read only memory (ROM), disk drive, tape drive, etc., or a combination thereof. The present invention can be implemented as a module (block 807) of the CPU or a routine stored in memory (block 803) and executed by the CPU (block 802) to process input data (block 808). For example, the data may include image information from a camera, which may be stored to memory (block 803) As such the computer system (block 801) is a general purpose computer system that becomes a specific purpose computer system when executing the routine of the present disclosure. The computer system (block 801) may further include a GPU (block 809) for image processing.

The computer platform (block 801) also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the system is programmed. Given the teachings of the present disclosure provided herein, one of ordinary skill in the related art will be able to contemplate these and similar implementations or configurations of the present disclosure.

Having described embodiments for visualizing brain network connectivity, it is noted that modifications and variations can be made by persons skilled in the art in light of the above teachings. It is therefore to be understood that changes may be made in embodiments of the present disclosure that are within the scope and spirit thereof.

What is claimed is:
1. A method for visualizing brain network connectivity in 3-dimensions (3D), comprising:
receiving image data corresponding to a brain of interest;
constructing a brain network from the image data by recursively clustering network nodes using knowledge of brain networks, wherein centroids of hierarchical clusters are determined and used as nodes to construct hierarchical brain networks to guide connections of a target network of the whole brain, wherein edges are started from leaf nodes and then converged toward ancestor nodes;
rendering edges between nodes using B-Spline curves constructed from control points found by searching for a nearest common ancestor of two related nodes of the target network from the hierarchical brain networks;
duplicating at least one control point for spline edges sharing a common ancestor to create an extra copy of said at least one control point;
bundling spline edges by applying a global strength parameter β;
displaying a 3D visualization of the brain network connectivity by rendering left/right view images into a frame buffer object (FBO) at full screen resolution, and attaching content from the FBO as textures to a corresponding viewer or viewers; and
coloring edges by an alpha blending technique that blends a color of a start node and a color of an end node, wherein a local blending factor is a normalized distance to the start node and a global blending factor is a normalized line length.

2. The method of claim 1, wherein the brain network is a tree data structure, the tree data structure comprises
a plurality of layers including a top layer having a first vertex corresponding to an entirety of the image data,
a bottom layer comprising second vertices corresponding to the plurality of network nodes, and
a plurality of intermediate layers comprising third vertices corresponding to a clustered region,
wherein each network node is connected to a root of the tree data structure.

3. The method of claim 2, further comprising rendering a ring of a radial layout depicting the tree data structure, wherein a plurality of vertices may be traversed from the top to the bottom, wherein a segment size of the ring is proportional to a number of vertices at the bottom layer in a corresponding tree branch, and displaying a visualization of the brain network connectivity in the radial layout including bundled spline edges.

4. The method of claim 1, further comprising applying a mono color for connection spline edges.

5. The method of claim 1, further comprising determining a color value for each spline edge by a linear interpolation using a length of the corresponding spline edge.

6. The method of claim 1, wherein constructing the brain network from the image data comprises
determining a structural connectivity of the brain of interest,
wherein the brain network depicts the structural connectivity of the brain of interest.

7. The method of claim 1, wherein constructing the brain network from the image data comprises
determining a functional connectivity of the brain of interest,
wherein the brain network depicts the functional connectivity of the brain of interest.

8. The method of claim 1, wherein the image data is obtained by one of molecular diffusion, resting-state functional magnetic resonance imaging, magnetoencephalography and electroencephalography.

9. The method of claim 1, wherein constructing the brain network from the image data is performed using a brain atlas.

10. The method of claim 1, wherein constructing the brain network from the image data includes recursively clustering highly interconnected nodes that are sparsely connected to nodes in other clusters.

11. A non-transitory program storage device readable by a computer, encoded with a program of instructions executed by the computer to perform the method steps for visualizing brain connectivity in 3-dimensions (3D), the method comprising the steps of:
receiving image data including molecular diffusion of a brain of interest;
constructing a brain network from the image data by recursively clustering network nodes using knowledge of brain networks, wherein centroids of hierarchical clusters are determined and used as nodes to construct hierarchical brain networks to guide connections of a target network of the whole brain, wherein edges are started from leaf nodes and then converged toward ancestor nodes;
rendering edges between nodes using B-Spline curves constructed from control points found by searching for a nearest common ancestor of two related nodes of the target network from the hierarchical brain networks;
duplicating at least one control point for spline edges sharing a common ancestor to create an extra copy of said at least one control point;
bundling spline edges by applying a global strength parameter β; and
displaying a 3D visualization of the brain network connectivity by rendering left/right view images into a frame buffer object (FBO) at full screen resolution, and attaching content from the FBO as textures to a corresponding viewer or viewers,
wherein constructing the brain network from the image data includes recursively clustering highly interconnected nodes that are sparsely connected to nodes in other clusters.

12. The computer program product of claim 11, wherein the brain network is a tree data structure, the tree data structure comprises
a plurality of layers including a top layer having a first vertex corresponding to an entirety of the image data,
a bottom layer comprising second vertices corresponding to the plurality of network nodes, and
a plurality of intermediate layers comprising third vertices corresponding to a clustered region,
wherein each network node is connected to a root of the tree data structure.

13. The computer program product of claim 12, the method further comprising rendering a ring of a radial layout depicting the tree data structure, wherein a plurality of vertices may be traversed from the top to the bottom, wherein a segment size of the ring is proportional to a number of vertices at the bottom layer in a corresponding tree branch, and
displaying a visualization of the brain network connectivity in the radial layout including bundled spline edges.

14. The computer program product of claim 11, further comprising applying a mono color for connection spline edges.

15. The computer program product of claim 11, further comprising determining a color value for each spline edge by a linear interpolation using a length of the corresponding spline edge.

16. The computer program product of claim 11, the method further comprising coloring edges by an alpha blending technique that blends a color of a start node and a color of an end node, wherein a local blending factor is a normalized distance to the start node and a global blending factor is a normalized line length.

17. The computer program product of claim 11, wherein constructing the brain network from the image data comprises
determining a structural connectivity of the brain of interest,
wherein the brain network depicts the structural connectivity of the brain of interest.

18. The computer program product of claim 11, wherein constructing the brain network from the image data comprises
determining a functional connectivity of the brain of interest,
wherein the brain network depicts the functional connectivity of the brain of interest.

19. The computer program product of claim 11, wherein the image data is obtained by one of molecular diffusion, resting-state functional magnetic resonance imaging, magnetoencephalography and electroencephalography.

20. The computer program product of claim 11, wherein constructing the brain network from the image data is performed using a brain atlas.

* * * * *